US011543508B2

(12) United States Patent
Rothwell et al.

(10) Patent No.: US 11,543,508 B2
(45) Date of Patent: Jan. 3, 2023

(54) SYSTEM AND METHOD FOR TIME-GAIN COMPENSATION CONTROL

(71) Applicant: FUJIFILM Sonosite, Inc., Bothell, WA (US)

(72) Inventors: Jason Rothwell, Shoreline, WA (US); Andrew Lundberg, Woodinville, WA (US); Jean Tsou, Seattle, WA (US); Craig Chamberlain, Seattle, WA (US); Wendy Swan, Lake Forest Park, WA (US); Brittney Klingenberg, Snohomish, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 1013 days.

(21) Appl. No.: 16/205,622

(22) Filed: Nov. 30, 2018

(65) Prior Publication Data

US 2020/0174108 A1 Jun. 4, 2020

(51) Int. Cl.
| | | |
|---|---|---|
| *G01S 7/52* | (2006.01) | |
| *A61B 8/00* | (2006.01) | |
| *G01S 15/89* | (2006.01) | |
| *G06F 3/04847* | (2022.01) | |
| *G06F 3/04883* | (2022.01) | |

(52) U.S. Cl.
CPC .......... *G01S 7/52033* (2013.01); *A61B 8/461* (2013.01); *A61B 8/467* (2013.01); *A61B 8/54* (2013.01); *G01S 7/52053* (2013.01); *G01S 15/8906* (2013.01); *G06F 3/04847* (2013.01); *G06F 3/04883* (2013.01); *G06F 2203/04808* (2013.01)

(58) Field of Classification Search
CPC ............ G01S 7/52033; G01S 7/52053; G01S 15/8906; G01S 7/52084; A61B 8/461; A61B 8/467; A61B 8/54; A61B 8/463; A61B 8/565; G06F 3/04847; G06F 3/04883; G06F 2203/04808
See application file for complete search history.

(56) References Cited

U.S. PATENT DOCUMENTS

2015/0359516 A1\* 12/2015 Yang .................. G06F 3/04847
600/443
2020/0174108 A1\* 6/2020 Rothwell ............ G06F 3/04847

FOREIGN PATENT DOCUMENTS

| WO | WO-2010051587 A1 \* | 5/2010 | ............... A61B 8/00 |
| WO | WO-2020112644 A1 \* | 6/2020 | ............. A61B 8/461 |

\* cited by examiner

*Primary Examiner* — Daniel Pihulic
(74) *Attorney, Agent, or Firm* — Baker Botts L.L.P.

(57) ABSTRACT

Certain embodiments include an apparatus, system, or method for time-gain compensation control of an ultrasound system. A computer-implemented method can include providing a tactile gain control comprising a near, middle, and far gain control. The middle gain control can be configured for two-dimensional range adjustment of depth and gain. The computer-implemented method can also include adjust at least one of the near, middle, or far gain control. In addition, the computer-implemented method can include displaying an ultrasound image based on at least one of the adjusted near, middle, or far gain control.

22 Claims, 10 Drawing Sheets

SYSTEM AND METHOD FOR TIME-GAIN COMPENSATION CONTROL

BACKGROUND

Non-stationary medical imaging devices, such as ultrasonic diagnostic instruments and related equipment, often referred to as ultrasound imaging systems, or simply as ultrasound systems, provide users with the ability to generate images of internal organs. To generate an image, a transducer of the ultrasound system generates and transmits a signal. The signal can be a sound pulse which propagates through the human body as a sound wave. As the sound waves travel through the body, the waves attenuate and reflect back towards the transducer.

The strength of the reflected sound waves can vary depending on when they are reflected, and the part of the body they travel through. Signals that are reflected after traveling a very short distance from the surface of the body can generally be strong, while signals that are reflected after traveling a long distance from the surface of the body can generally be weak. Due to the varying signal strength, the front end of the ultrasound system that receives the signals can be equipped with amplifiers and controllers for normalizing the received signals. The amplifier, which may be a highly linear low noise amplifier, for example, can be used to amplify weak signals, while the controllers can help to ensure that the strong signals do not distort the other received signals.

Once the sound signals are received at the transducer, the signals can be intelligently summed and scaled to create an image of the internal organs. The image displayed to the user will appear to have variable brightness, with those parts represented by stronger signals appearing brighter, and those parts represented by weaker signals appearing darker. To help compensate for the effect of signal attenuation due to distance traveled through the body, ultrasound systems can include a Time Gain Control (TGC), which may be applied on the front end of the ultrasound system by adjusting analog and/or digital gain as a function of time/depth. TGC may apply variable amplification to the received signals according to the return time of the signals. Adjusting the TGC will help users to achieve the desired brightness of the ultrasound image regardless of depth. The adjustment will allow a displayed ultrasound image to appear uniform in homogenous tissue, even though the signal decreases as depth increases.

Ultrasound systems can include sliders, knobs, and/or up or down button controls that allow users to manually adjust the time gain, which may simply be referred to as gain, of an ultrasound image. Each manual slider can be assigned to a particular depth, and allow users to adjust the time gain at the particular depth. Knobs may also be used for near or far gain control, where near represents a skin line depth and far represents the deepest displayed depth on the image. Such manual sliders, however, only provide for limited gain adjustment, without providing the user any control over the actual gain curve. In addition, the manual sliders allow novice users, for example, to have too much control of the gain, while also requiring frequent adjustment to undo previous adjustments made for prior users or subjects. The use of manual sliders may therefore be time consuming, while also being difficult to clean.

SUMMARY

The disclosed subject matter described below provides for a non-limiting example of an improved ultrasound imaging system and method which can address the problems identified and others. For example, embodiments of the disclosed subject matter can provide time-gain compensation control for a medical imaging device, such as an ultrasound system. The improved time-gain compensation control may provide for increased customization, allowing users further control of the gain curve.

An example computer-implemented method in an ultrasound system can be used for providing a tactile gain control comprising a near, middle, and far gain control. The middle gain control can be configured for two-dimensional range adjustment of depth and gain. The computer-implemented method in the ultrasound system can also include adjusting at least one of the near, middle, or far gain control. In addition, the computer-implemented method in the ultrasound system can include displaying an ultrasound image based on at least one of the adjusted near, middle, or far gain control.

In another example, an ultrasound system can include at least one memory comprising computer program code, and at least one processor. The computer program code can be configured, when executed by the at least one processor, to cause the ultrasound system at least to provide a tactile gain control comprising a near, middle, and far gain control. The middle gain control can be configured for two-dimensional range adjustment of depth and gain. The computer program code can also be configured, when executed by the at least one processor, to cause the ultrasound system at least to adjust at least one of the near, middle, or far gain control. In addition, the computer program code can be configured, when executed by the at least one processor, to cause the ultrasound system at least to display an ultrasound image based on at least one of the adjusted near, middle, or far gain control.

According to certain embodiments a non-transitory computer-readable medium encodes instructions that, when executed in hardware, perform a process. The process can include providing a tactile gain control comprising a near, middle, and far gain control. The middle gain control can be configured for two-dimensional range adjustment of depth and gain. The process can also include adjusting at least one of the near, middle, or far gain control. In addition, the process can include displaying an ultrasound image based on at least one of the adjusted near, middle, or far gain control.

An apparatus, in certain embodiments, can include a computer program product encoding instructions for performing a process according to a method. The method may include providing a tactile gain control comprising a near, middle, and far gain control. The middle gain control can be configured for two-dimensional range adjustment of depth and gain. The method can also include adjusting at least one of the near, middle, or far gain control. In addition, the method can include displaying an ultrasound image based on at least one of the adjusted near, middle, or far gain control.

DETAILED DESCRIPTION

Figure 1:
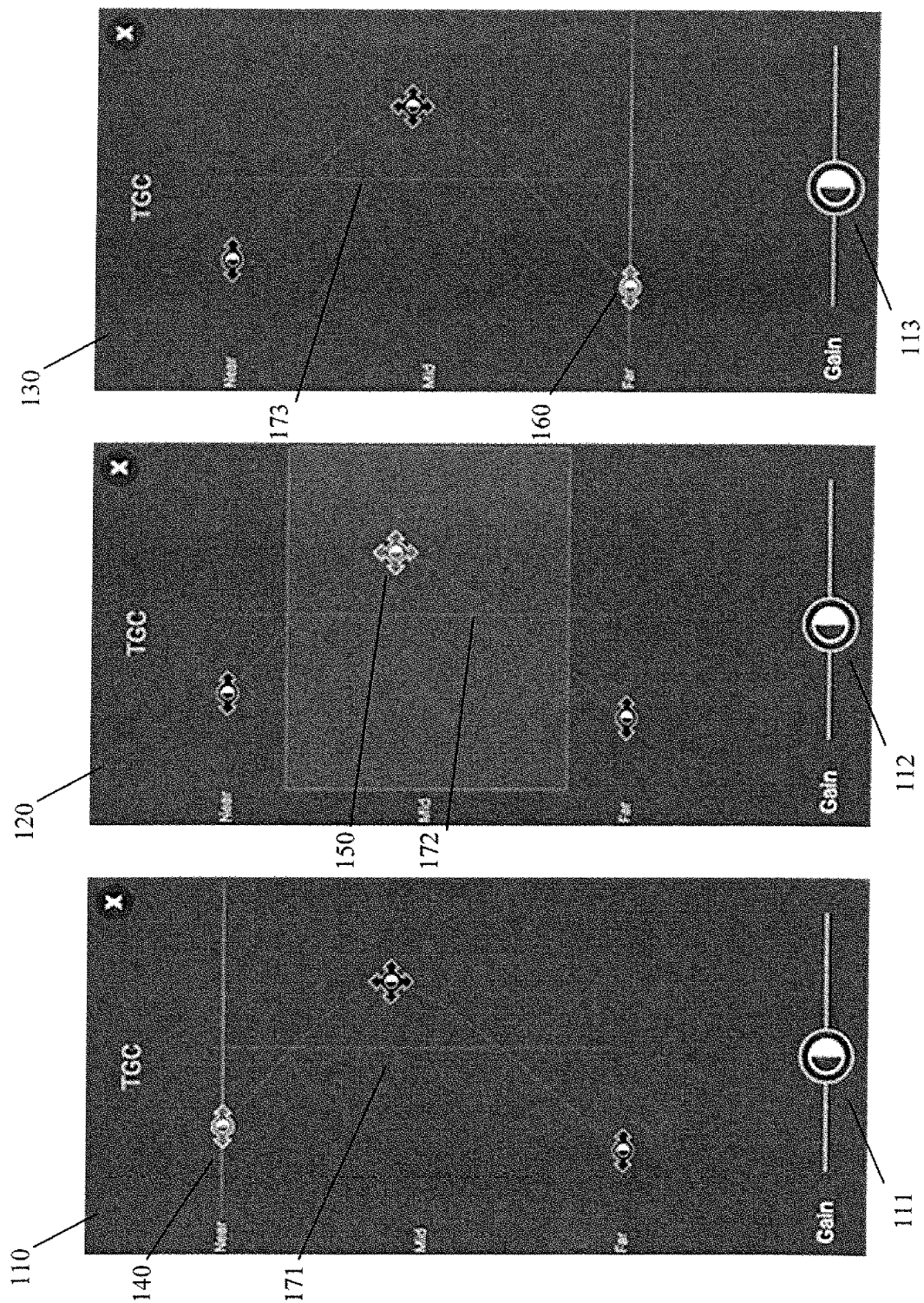
FIG. 1 is a diagram illustrating a user interface according to some embodiments of the disclosed subject matter.

Reference will now be made in detail to the various exemplary embodiments of the disclosed subject matter, which embodiments are illustrated in the accompanying drawings. The structure and corresponding method of operation of the disclosed subject matter will be described in conjunction with the detailed description of the system. The examples and embodiments described below are merely exemplary, and should not be taken in any way as limiting the scope of the disclosed subject matter.

In certain embodiments, an ultrasound system may be provided with TGC. The TGC allows users to adjust the gain of an ultrasound image to achieve a desired image. The purpose of TGC may be to normalize signal amplitude with time, thereby allowing for depth compensation. Some ultrasound systems are provided with a tactile gain control that includes near, far, and overall gain controls. Near gain controls can be configured to attenuate or amplify sound pulses that are reflected closer to the body surface. In other words, near gain control may represent at least an area at or near the skin line. In some embodiments, the gain at the skin line may be the same as the gain at a determined near point. The signals manipulated by the near gain controls can be stronger and can appear brighter on the ultrasound system display.

Far gain controls can be configured to attenuate or amplify pulses that are reflected further away from the body surfaces. In other words, far gain control may represent at least the furthest distance the sound will travel from the face of the transducer, or the deepest depth of the displayed image. The maximum depth may be determined based on the transducer or transducer type being used. Such signals manipulated by the far gain controls can be weaker and can appear darker on the ultrasound system display. The far signals can be reflected back to the transducer in a point in time after the near signals are reflected back to the transducer. In certain embodiments, the far and near gain control may allow for controlling the gain at the beginning and end of the signal.

The overall gain control, on the other hand, can be used to adjust the entire received signals together, as opposed to only adjusting the gain of signals received from a given depth. In other words, the gain can be adjusted using an overall gain control that is separate from the near and far gain controls.

Providing users with overall, near, and far gain controls allows users to perform a limited adjustment of the gain, while forcing the user to accept an approximation of the gain profile. This approximation of the gain profile sometimes does not provide users with the ability to customize an ultrasound image according to their preferences. Certain embodiments, therefore, provide a middle gain control. The middle gain control can allow users to control those signals falling between the near and far signals. The middle gain control may be implemented as a boundary box, which controls the distance or depth a user can control gain. The boundary box can define the limits of the middle gain control, in certain embodiments, preventing the user from adjusting the gain or depth beyond the allowable limits of the boundary box. The horizontal upper limit of the boundary may be determined by the near gain control, while the horizontal lower limit of the boundary may be determined by the far gain control.

Adding the middle gain control may provide an additional point of control for the user, allowing for a more accurate gain profile to be controlled by a user. The middle gain control can allow for increased customization of an ultrasound image. Using the middle gain control, a complex gain curve may be calculated, as opposed to a linear calculation using merely the near and far gain control.

In some embodiments, the middle gain control may be configured for two-dimensional range adjustment. The two-dimensional range adjustment may comprise both a depth adjustment and a gain adjustment. In other words, the middle gain control can allow for a two-dimensional range adjustment of depth and gain. Using the tactile gain control, which comprises near, middle, and far gain controls, a gain curve can be determined. The image displayed by the ultrasound system may be based on the determined gain curve.

FIG. 1 is a diagram illustrating a user interface according to some embodiments of the disclosed subject matter. Specifically, FIG. 1 illustrates an ultrasound system with a near, middle, and far gain control. In certain embodiments, the adjustment of the near, middle, and far gain control may be activated by touching a button or surface on the system control panel. For example, a tactile gain control may be activated in response to a received user input. The received user input may be a sensed touching of the tactile gain control by a user.

The tactile gain control may include the near, middle, and/or far gain control, and may be a touchscreen interface or a trackpad located on the system control panel, on a display screen, or on any other part of the ultrasound system. A user may then use their finger to adjust a digital handle on the touchscreen to adjust any one of the near, middle, or far gain. In yet another embodiment, the tactile gain control may be a slider, handle, knob, thumbstick, button, or any other physical controller. In some embodiments, one or more controllers can be used to control each of the near, far, middle, and overall gain. In yet another embodiment, the controllers may be controlled by touchless commands, such as voice commands. Adjusting the near, far, middle, or overall gain using the above controls may be referred to as adjusting the near, far, middle, or overall gain control. The at least one of the near, middle, or far gain control may be adjusted based on a received user input, where the received user input, for example, may be a sensed touching of a user interface.

In certain embodiments, there may be a mapping between a movement distance of the near, middle, and far gain control on the user interface, and the amount of gain change. The amount of gain curve that may be mapped to a physical distance on the machine interface may be based on the system type, transducer type, imaging mode, and/or examination type. The imaging modes, for example, may be a two-dimensional, color, pulse-wave doppler mode, and/or any other mode. For example, in a two-dimensional mode a half an inch movement distance on the user interface may be equivalent to 9 or 10 decibels (dBs). In another example, in a steep needle profiling mode a half an inch movement distance on the user interface may be equivalent to 4.5 dBs. Any other mapping of the gain control to the amount of gain change may be possible. When the full width of the controllable area changes, the gain per distance on the user interface may be adjusted accordingly.

As shown in FIG. 1, the vertical axis of the user interface may represent depth of the received signal, while the horizontal axis may represent the gain. Each of the near, middle, and far gain control may be independently moved. The near and far gain controls may correspond to a fixed depth for a given state, and may be moved to adjust the gain. The middle gain control, on the other hand, may be moved in two dimensions, with a horizontal movement representing gain and a vertical movement representing time and/or depth. User interface 110 may illustrate adjustment of the near gain control. Activating the near gain control may involve using any of the controls explained above. In one non-limiting example, activation may involve touching of a digital near gain control handle on a touchscreen or trackpad located on system control panel. The near, far, middle, or overall gain control may also be activated by touching a digital handle or button on a touchscreen or trackpad located on system control panel.

When the near gain control is active, as shown in 140, the adjustment range may be highlighted on the user interface. The near gain control may be adjusted horizontally on a gain axis to increase or decrease gain at the set near depth between a minimum and a maximum gain value. In one example, the minimum value may be 0 dBs, while the maximum value may be 20 dBs. In the example shown in FIG. 1, a user interface 110 may restrict the movement of the near gain control to horizontal movement. Adjusting the near gain control may also adjust the gain curve. The gain curve can be seen in user interface 110 as the curve connecting the near, middle, and far gain control.

User interface 120 illustrates a user interface in which the middle gain is active. In user interface 120, when the middle is active, as shown in 150, the possible vertical and horizontal range can be highlighted in the form of a boundary box. Vertical movement of the middle gain control may represent a time and/or depth adjustment, while horizontal movement may represent gain adjustment. Because the middle gain control may be adjusted in a two-dimensional range, the highlighted range may be shown as a square or rectangular highlighted area. The upper limit of the highlighted area may be the near control, while the lower limit of the highlighted area may be the far control.

In addition to the two-dimensional vertical and horizontal movement, the middle gain control may also be rotated. Rotation in some embodiments may be clockwise, while rotation in other embodiments may be counterclockwise. Rotating the middle gain control may adjust the curvature of the gain curve. In certain embodiments, the clockwise rotation tightens the curvature being displayed on the user interface. As described above, the rotation may adjust or twist the curvature of the gain curve, which can allow for greater control of the gain curve. For example, as a default the gain curve may be a parabola or hyperbola, drawn from the near gain control point to the far gain control point, as shown in FIG. 1. Rotating the middle gain control may change the gain curve to a cosine or sine curve, drawn from the near gain control point to a far gain control point.

To rotate the middle gain control, a user may use a two-finger twist gesture. The two-finger twist gesture may involve placing two fingers on the touch screen user interface, for examples, and twisting the fingers either clockwise or counter clockwise. In certain other embodiments, any other finger gesture or movement may trigger rotation of the middle gain control. In some other embodiments, a button, lever, or handle on the system control panel may trigger rotation of the middle gain control.

Although the example illustrated in user interface 120 only includes a single middle gain control, certain other embodiments may include more than one middle gain control. Providing more than one middle gain control may allow for increased customization by the user. Each middle gain control may be assigned a predetermined depth range so that the one or more middle controls do not cross each other, allowing for two-dimensional movement of the middle gain control within the predetermined depth range.

User interface 130 illustrates adjustment of the far gain control. When the far gain control is active, as shown in 160, the adjustment range may be highlighted on the user interface. The far gain control shown in user interface 130 may be horizontally adjusted between a minimum and a maximum value. In one example, the minimum value may be 0 dBs, while the maximum value may be 20 dBs. The minimum and maximum values be determined based on the technical capabilities of the transducer, or any other part of the ultrasound system.

As illustrated in user interfaces 110, 120, and 130, a gain curve may connect the near, middle, and far gain control. The curve joining the handles of the near, middle, and far gain controls may provide the user with a clear view of the displayed overall gain curve. In certain embodiments, the gain may be reset, allowing the user to return the image to a baseline setting or a default setting. For example, the baseline setting may be predetermined to be a vertical gain reference line, such as 171, 172, and 173. In some embodiments, to reset the gain a user may double-tap the vertical gain reference line or the displayed gain curve. In some other embodiments, the user may perform the reset using any other user input, such as using a touch or gesture on the touchscreen or touchpad to adjust the gain control. For example, a long touch, a vertical swiping motion from top to bottom or from bottom to top, and/or a touching of a specific area on the gain tactile interface may be used to reset the gain control. In some other embodiments, the reset may be performed by pressing a button on the system control panel or the user interface.

In certain embodiments the baseline setting may reflect a gain curve shown on the user interface, representing the near, middle, and far gain control being displayed in a vertical middle position. In certain other embodiments, however, the baseline setting may represent a gain curve that is non-linear. The baseline setting may be based on, for example, the body part being imaged, the type of examination, or the person being imaged. In one example, the baseline setting may depend on the tissue interface. In other words, while the near, middle, and far gain controls may appear to a user to be set in a vertical middle position, the underlying gain curve may be different than a linear gain curve. The baseline gain curve may be determined by image optimization where the gain curve may compensate for tissue attenuation, beam forming intensity profile, and/or noise control.

In one non-limiting example, an overall gain control that is separate from the near, middle, or far gain control may be provided. In some embodiments, an overall gain slider or button at the bottom of the panel may shift the whole gain curve to the left or right. User interfaces 110, 120, and 130 may respectively include overall gain sliders 111, 112, and 113. Overall gain sliders 111, 112, and 113 may take the form of a circular button capable of sliding between a minimum and a maximum value.

The horizontal and/or vertical position of the near, middle, and far gain control, as well as the rotational orientation of the middle gain control, may be communicated to the ultrasound control system. The ultrasound control system may be a central processing unit or a processor located within the ultrasound system. The central processing unit or processor may determine or calculate a gain curve based on the near, middle, and far gain control. The ultrasound image may be displayed in the ultrasound system based on the gain curve.

To determine or calculate the gain curve, any type of interpolation may be used, with the near, middle, and far gain serving as the data point for the calculation. The interpolation may be based on at least one of a transducer type, an imaging mode, and/or an examination type. For example, a piecewise cubic hermit interpolating polynomial (pchip), such as a piecewise cubic spline, may be used. Using pchip, the curve goes through all control points, and the gain change matches the slider position change. In some other embodiments, any other interpolation may be used. The type of interpolation may be chosen based on an adjustment sensitivity of a specific application. For example, Bézier curve fitting may be used when the user moves the slider with a greater distance to make a small gain adjustment.

As discussed above, in some embodiments the near and far gain control may be adjusted between a minimum value and a maximum value. The minimum and maximum value may reflect the allowable values that the ultrasound system may be capable of processing or a self-imposed limit of amplification. The middle gain control, on the other hand, may be adjusted on the user interface by a user to reflect a gain curve that may be beyond the technical capabilities of the ultrasound system. The technical capabilities may be based on the hardware used by the ultrasound system. While the hardware of the ultrasound system itself may impose a minimum or maximum, the middle gain control may be adjusted by the user to reflect values that go beyond such capabilities to achieve a desired gain curve. The ultrasound system may then limit the gain values that exceed the allowable maximum to the maximum, without having to adjust any of the other gain values.

Figure 2:
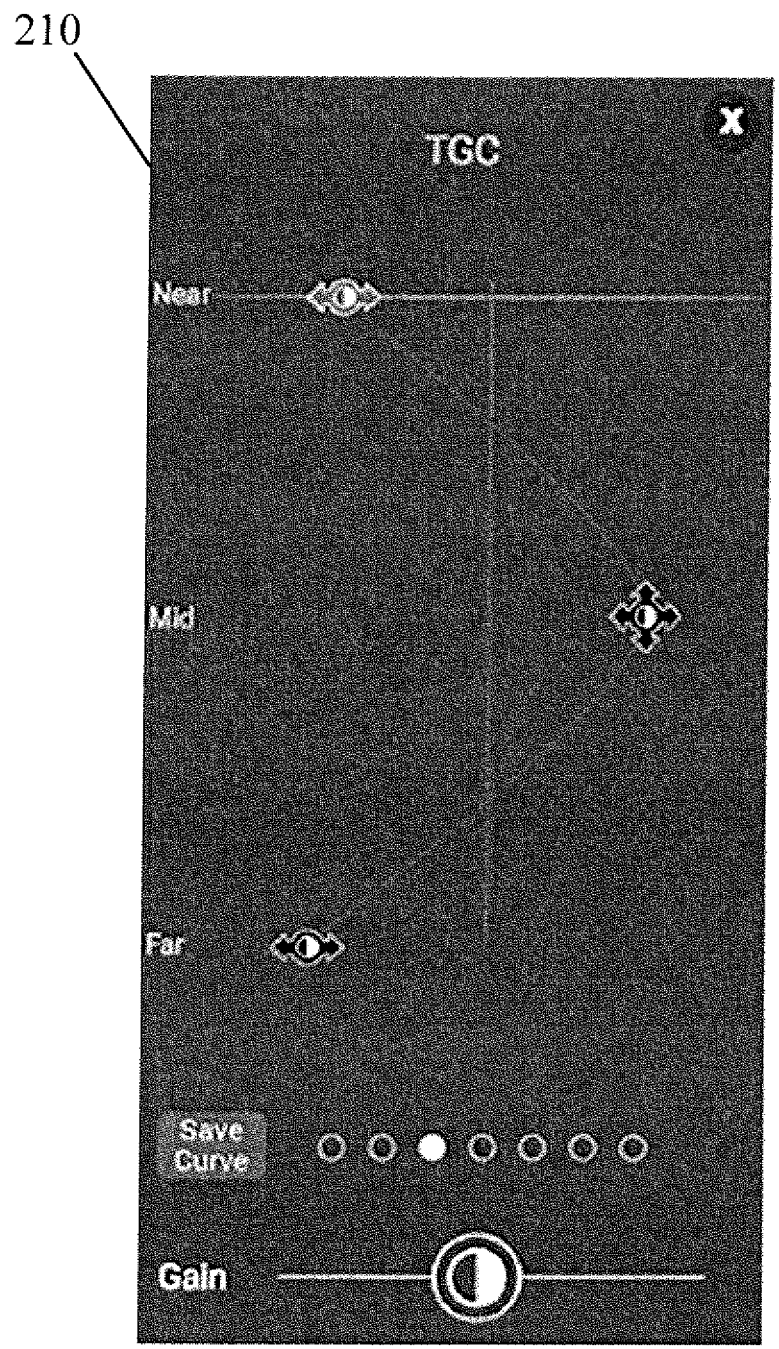
FIG. 2 is a diagram illustrating a user interface according to some embodiments of the disclosed subject matter.

FIG. 2 is a diagram illustrating a user interface according to some embodiments of the disclosed subject matter. In particular, FIG. 2 illustrates a user interface in which a user can store and select a gain profile. In certain embodiments, a stored gain profile may be retrieved by the ultrasound system based on a user selection. A given gain profile may be associated for a certain procedure or a particular location or organ in the body a user is imaging. For example, a first gain profile may be selected when a user is attempting to obtain an ultrasound image of a heart from one angle, while a second gain profile may be selected when the user is attempting to obtain another view of the heart. In certain embodiments, the gain profile may be set by the user based on at least one of the screen depth, type of exam, and/or transducer being used.

A gain profile includes a position of the near, middle, and far gain control, and/or the rotational orientation of the middle gain control. While some gain profiles may be preset, others may be manually created by the user. Once the horizontal and/or vertical position of the near, middle, and far gain control, as well as the rotational orientation of the middle gain control, are all set by the user, the user may press a button on the system control panel or on the touchscreen to save the gain profile. While user interface 210 merely illustrates that seven different gain profiles may be saved, in certain other embodiments any other number of gain profiles may be saved. To select a profile in user interface 210, a user may tap the dot associate with their preferred, saved gain profile. In other embodiments, the profile may be selected using any button or handle on the system control panel, or pressing any digital button or area on the touchscreen.

Figure 3:
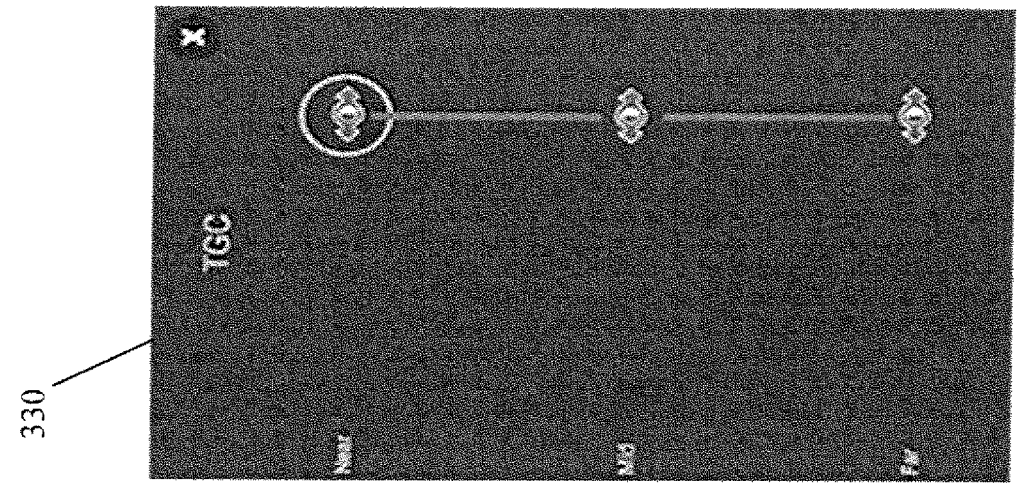
FIG. 3 is a diagram illustrating a user interface according to some embodiments of the disclosed subject matter.
Figure 3:
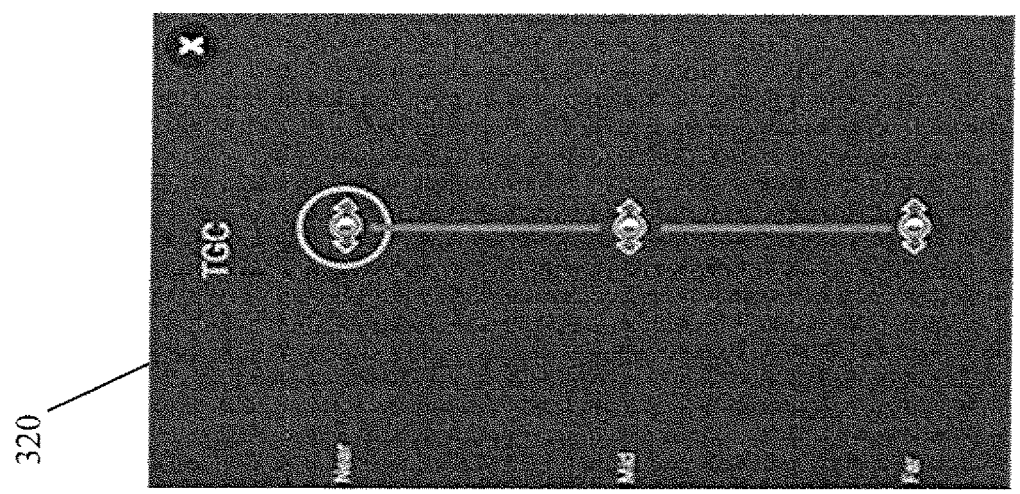
Figure 3:
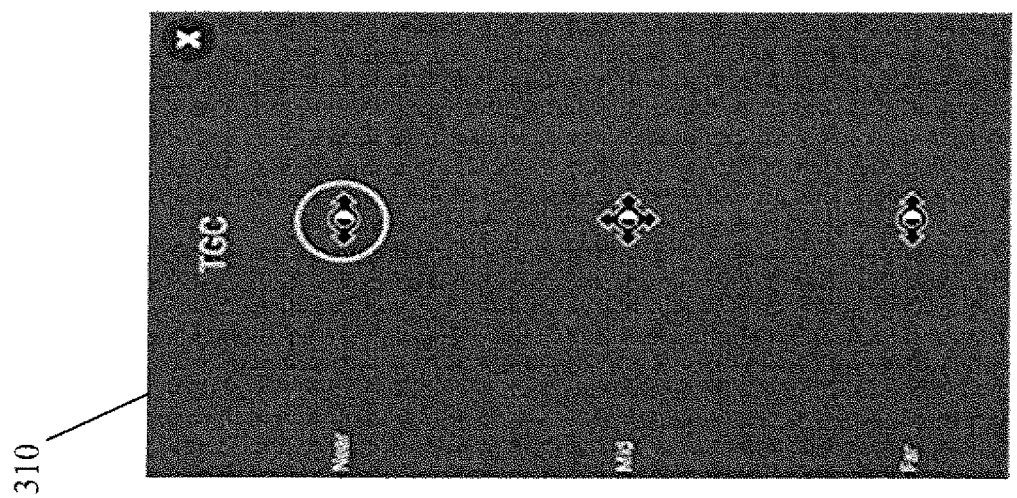

FIG. 3 is a diagram illustrating a user interface according to some embodiments of the disclosed subject matter. Specifically, FIG. 3 illustrates selecting and sliding an entire gain curve horizontally. In some embodiments, performing a touching action on a touchscreen may allow for moving the entire gain curve, which connects the near, middle, and far sliders, to the left or to the right, either decreasing or increasing the overall gain. The touching action, for example, may be a long press or a double tap on any of the near, middle, or far controls. In other embodiments, any other touching action on any one of the controls or on any other part of the touchscreen may activate movement of the entire gain curve.

In the example shown in FIG. 3, the movement of the entire gain curve may be activated by a long press or a double tap of the near gain control or slider, as shown in screen 310. The entire curve line may then be highlighted, as shown in screen 320, indicating that movement of the entire gain curve has been activated. A user may then move the curve with its current gain profile to the right, thereby increasing the gain, as shown in screen 330. In other words, the entire gain profile can be shifted to the right, uniformly increasing the gain for the entire gain curve.

Figure 4:
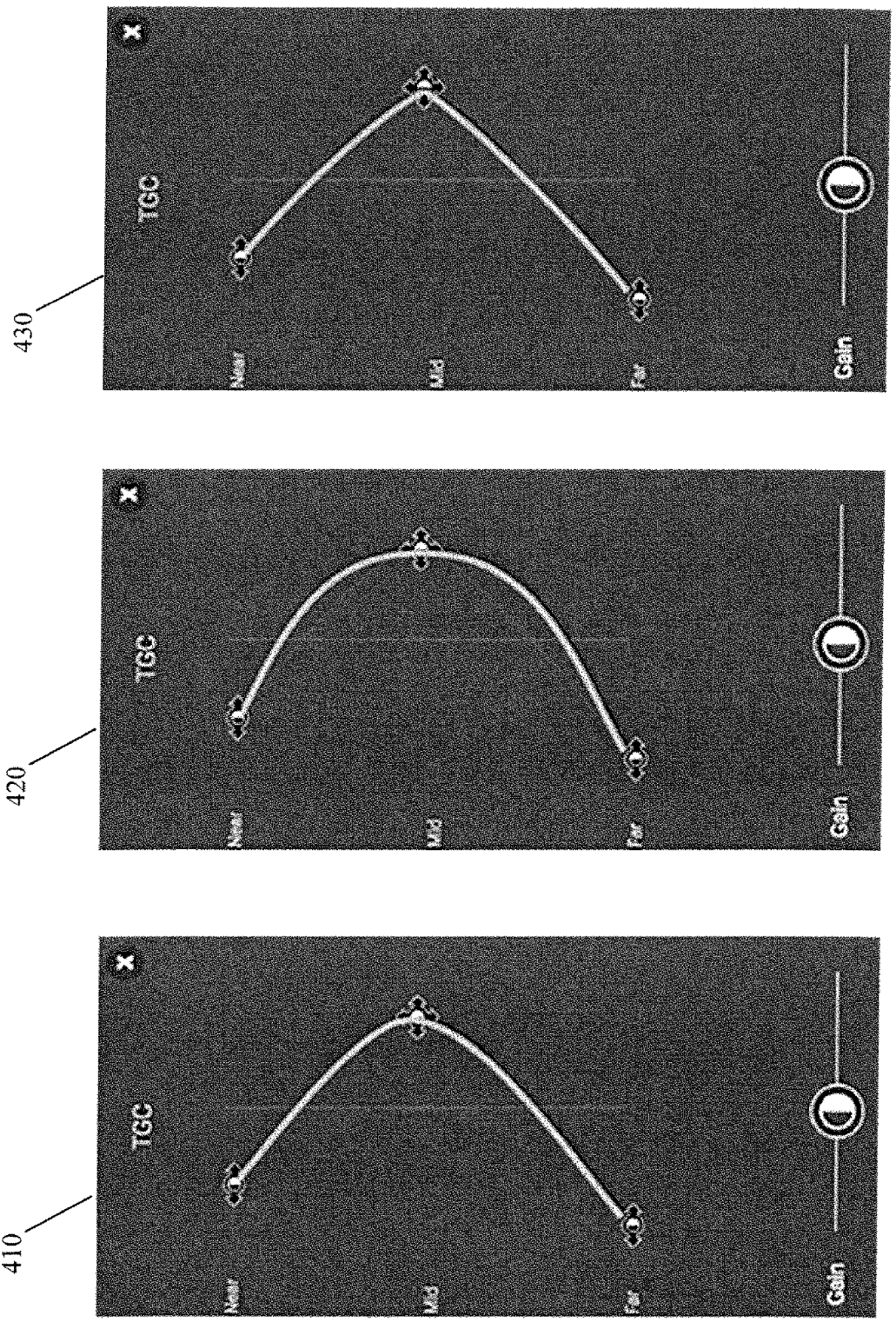
FIG. 4 is a diagram illustrating a user interface according to some embodiments of the disclosed subject matter.

FIG. 4 is a diagram illustrating a user interface according to some embodiments of the disclosed subject matter. Specifically, FIG. 4 illustrates adjusting the way the mid control impacts the gain curve above and below a control point. The adjusted impact of the mid control is referred to as a reach.

As shown in FIG. 4, a user may adjust the impact of the mid control above and below the control point on the gain curve. A user may tap the gain curve to reveal a visual indication of the mid control reach, as shown in user interface or screen 410. The gain curve illustrated in user interface or touch screen 410 illustrates the current reach setting of the mid control point. In one non-limiting example, the shape of the gain curve may change to reflect a different reach. In user interface or screen 420, reach may be increased by an opening pinch of the gain curve. In user interface or screen 430, the reach may be decreased by a closing pinch of the gain curve. In other words, in the example shown in FIG. 4 the reach may be increased by increasing the gain curve above and below the mid control point in a continuous manner, while the reach may be decreased by decreasing the gain curve above and below the mid control point in a continuous manner. While the above embodiments describe using a pinch to adjust the reach, any other gesture or button may be used to adjust the reach of the mid control point.

Figure 5:
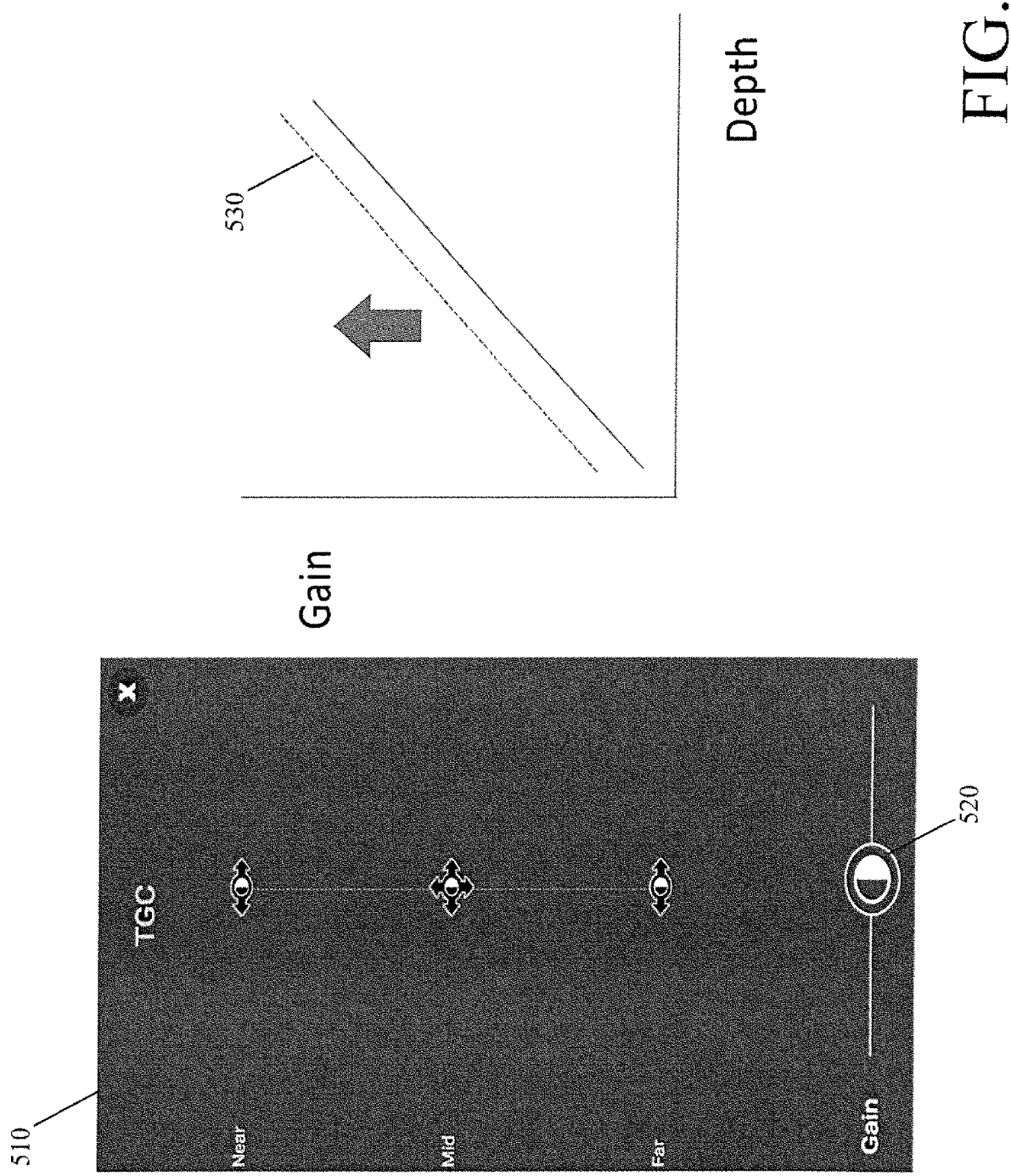
FIG. 5 is a diagram illustrating a user interface and gain curve according to some embodiments of the disclosed subject matter.

FIG. 5 is a diagram illustrating a user interface and gain curve according to certain embodiments of the disclosed subject matter. In particular, FIG. 5 illustrates an example embodiment of increasing the overall gain. For example, a user may shift or slide overall gain control 520 to the right using touch screen or user interface 510. Shifting or sliding the overall gain control 520 uniformly shifts the near, middle, and far gain control to the right, leading to a uniform increase in overall gain. As shown in FIG. 5, the resulting shift may uniformly increase gain curve 530. An overall gain control adjustment as illustrated in FIG. 5 may result in brightening of the entire ultrasound image displayed on the ultrasound system.

Figure 6:
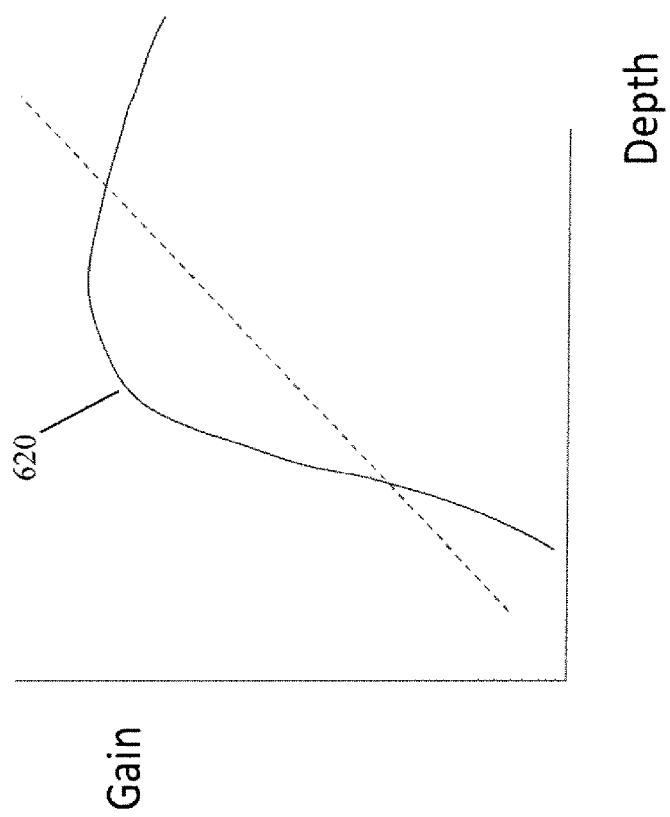
FIG. 6 is a diagram illustrating a user interface and gain curve according to some embodiments of the disclosed subject matter.
Figure 6:
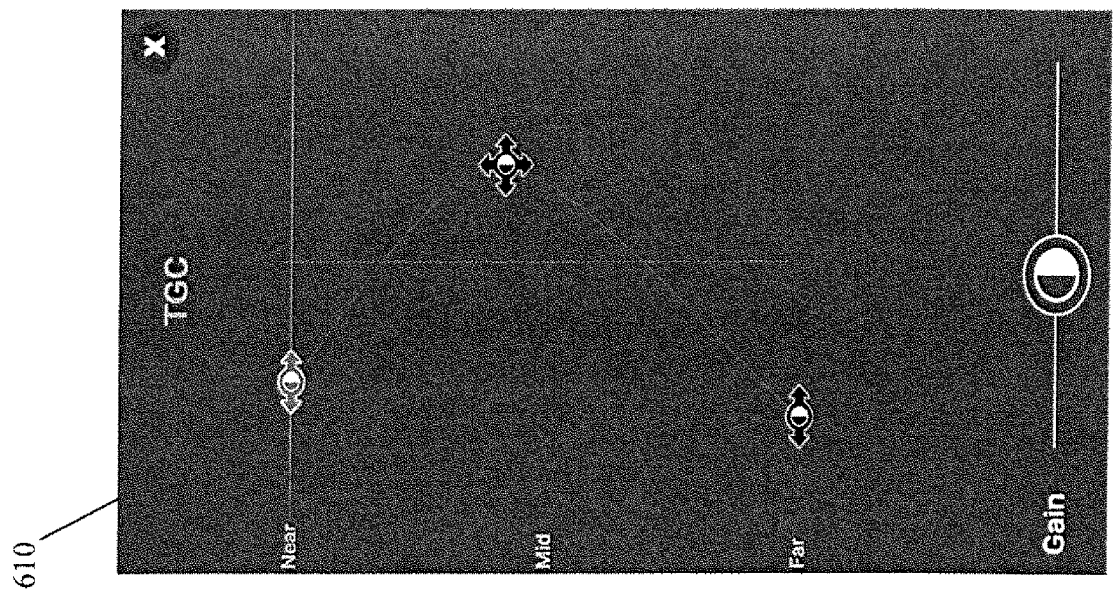

FIG. 6 is a diagram illustrating a user interface and gain curve according to certain embodiments of the disclosed subject matter. In particular, FIG. 6 describes an example embodiment of decreasing the near gain. For example, a user may adjust the near gain control by shifting or sliding the near gain control to the left, thereby reducing the gain at the near depth, as shown in gain curve 620. The near and far gain controls may be decreased from the original baseline location, while the middle gain control may be increased from the original baseline location. Such gain control adjustments are reflected in gain curve 620, with the near and far gain being below the baseline linear line, and the middle gain being above the baseline linear line. A near gain control adjustment as shown in FIG. 6 may result in the darkening of the top of the ultrasound image displayed on the ultrasound system, which represents the near depth.

Figure 7:
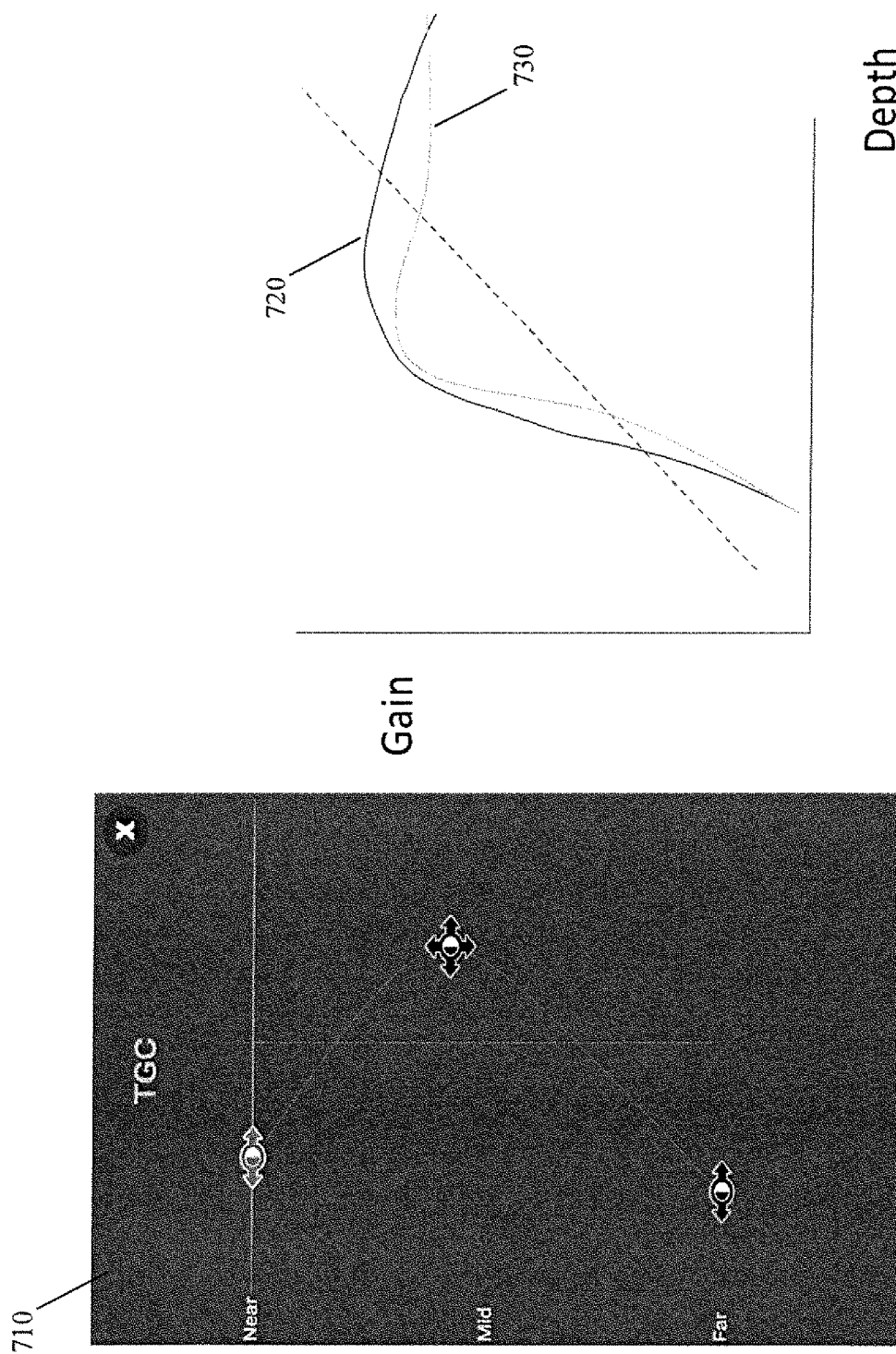
FIG. 7 is a diagram illustrating a user interface and gain curve according to some embodiments of the disclosed subject matter.

FIG. 7 is a diagram illustrating a user interface and gain curve according to certain embodiments of the disclosed subject matter. In particular, FIG. 7 describes an example embodiment of adjusting the near gain control while decreasing the reach of the mid control. As shown in user interface 710, the near gain control may be adjusted by shifting or sliding the control to the left, thereby reducing or decreasing the near gain. As shown in gain curve 720, the adjustment of the near gain control shown in user interface or screen 710 may result in gain reduction at the near depth. This near gain reduction may result in the darkening of the top of the ultrasound image, which represents the near depth.

The reach of the mid control in FIG. 7 may be decreased. As shown by gain curve 730, the slope of the gain curve 720 has been reduced in accordance with the pinching described in FIG. 4. The reduced reach of the mid control point may be reflected on the ultrasound image displayed by the ultrasound system by narrowing the bright middle area of the displayed ultrasound image, while only slightly reducing the brightness levels of the remaining middle area.

Figure 8:
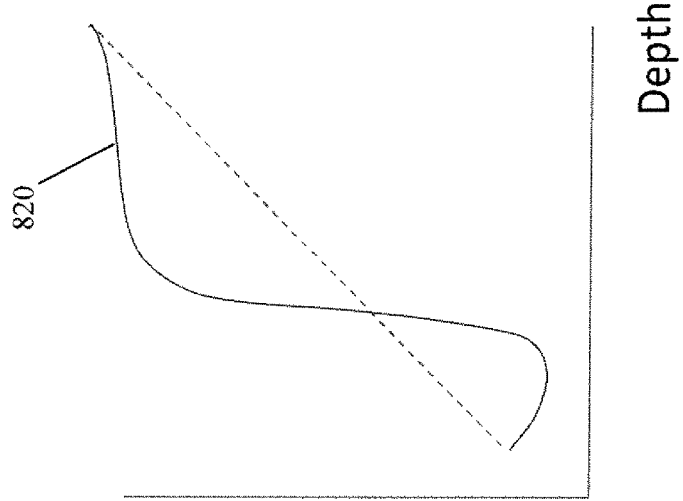
FIG. 8 is a diagram illustrating a user interface and gain curve according to some embodiments of the disclosed subject matter.
Figure 8:
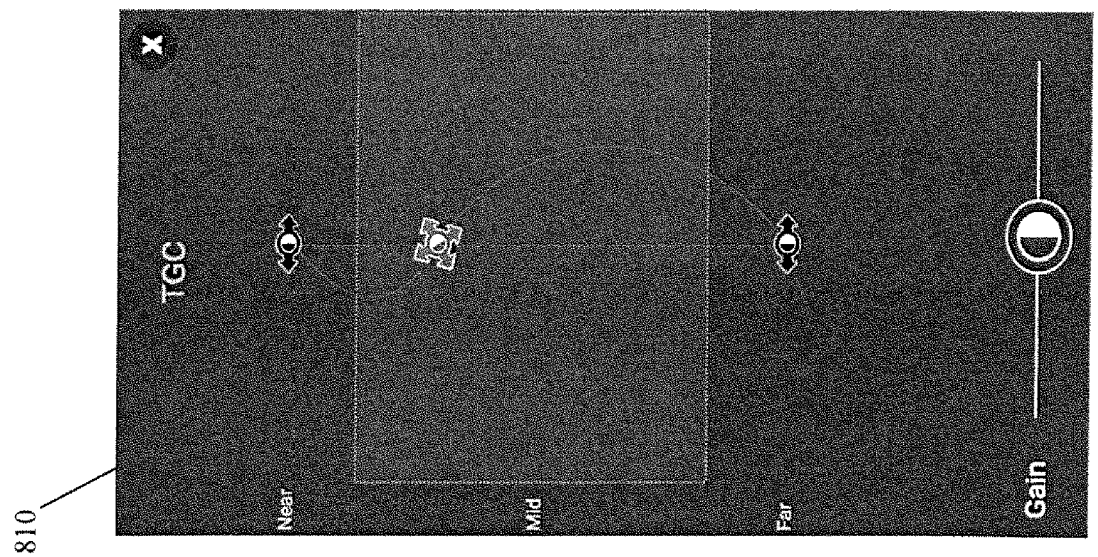

FIG. 8 is a diagram illustrating a user interface and gain curve according to certain embodiments of the disclosed subject matter. In particular, FIG. 8 illustrates an example embodiment of rotating the middle gain control. For example, a user may rotate the middle gain control shown in user interface or touch screen 810. Rotating the middle gain control may twist or change the slope of the gain curve. As shown in FIG. 8, rotating the middle gain control, either clockwise or counterclockwise, may twist or adjust the slope gain curve 820. In some other embodiments, rotation of the middle gain control may adjust any other characteristic of the gain curve. The rotation of the middle gain control may lead to a reduced brightness at the top of the ultrasound image, representing the near depth, while increasing the brightness of the middle and bottom of the ultrasound image, representing the middle and far depth.

Figure 9:
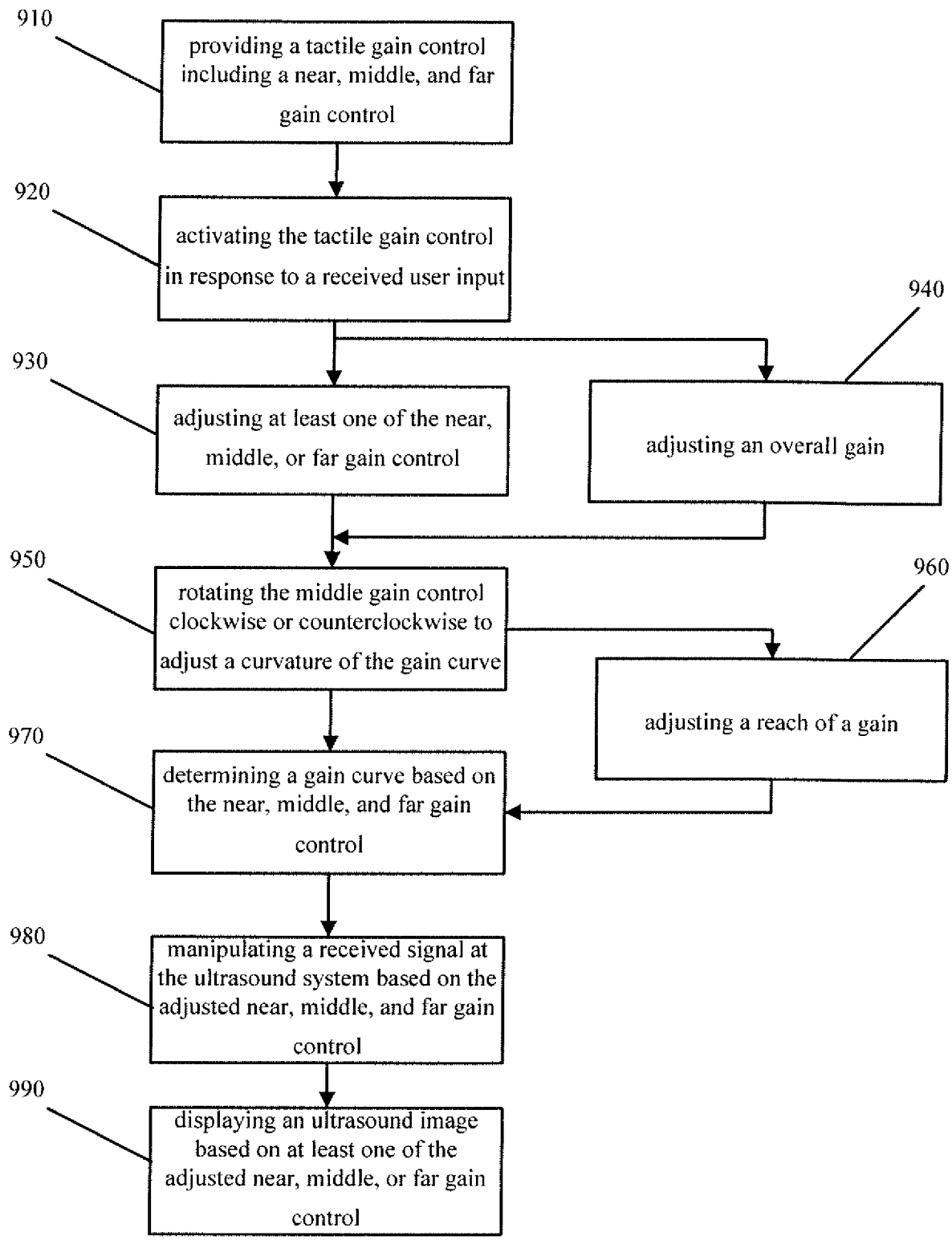
FIG. 9 is a flow diagram of a method or process according to some embodiments of the disclosed subject matter.

FIG. 9 is a flow diagram illustrating a method or process according to certain embodiments of the disclosed subject matter. In particular, FIG. 9 describes an example embodiment of a method or process performed by an ultrasound system for time-gain compensation control. In step 910, the ultrasound system may provide a tactile gain control comprising a near, middle, and far gain control. The middle gain control is configured for two-dimensional range adjustment of depth and gain. In certain embodiments, the near, middle, and far gain control may be activated in response to a received user input, as shown in step 920. The received user input may be a sensed touching of the tactile gain control by a user. The tactile gain control may be located on the system control panel and/or may be a touch user interface. In step 930, at least one of the near, middle, or far gain control may be adjusted. Alternatively, or in addition to, in step 940 the gain may be adjusted using an overall gain control that is separate from the near, middle, or far gain control. Each of the near, middle, or far gain controls can be individually adjusted.

In certain embodiments, the tactile gain control may be displayed on a user interface of the ultrasound system. The at least one of the near, middle, or far gain control may be adjusted based on a received user input. In one non-limiting example, the received user input may be a sensed touching of the user interface. The user interface, in some embodiments, may be a touch screen.

In step 950, the middle gain control may be rotated clockwise or counterclockwise to adjust the curvature of the gain curve. In some embodiments, the curve slope of the gain curve may be changed based on a received user input. As shown in step 960, the reach may be adjusted based on the changed curve slope. A gain reset configured to return the near, middle, and far gain control to a baseline setting may also be performed. In certain embodiments, a user input may be received at the tactile gain control to perform a gain reset. In one non-limiting example, the touching may include double tapping a vertical gain reference line or a displayed gain curve on the tactile gain control.

The gain curve may be determined based on the tactile gain control, as shown in step 970. The ultrasound image may be displayed based on the gain curve. In some embodiments, interpolation may be used for determining the gain curve. The interpolation may be based on at least one of a transducer type, an imaging mode, or an examination type. One non-limiting example may be a pchip. In step 980, the received signal at the ultrasound system may be manipulated based on the adjusted near, middle, and far gain control. The received signal may be manipulated at a beginning and an end of the signal. In step 990, the ultrasound image may be displayed based on at least one of the adjusted near, middle, or far gain control. The adjusted near, middle, or far gain control may change the brightness of the ultrasound image being displayed by the ultrasound system. In certain embodiments, the gain curve joining the near, middle, and far gain control may be displayed. The displayed gain curve may be different than an underlying gain curve used for manipulating a received signal at the ultrasound system.

In certain embodiments, a gain profile may be stored. The gain profile may include a position of the near, middle, and far gain control. The stored gain profile may be retrieved based on a user selection, and the ultrasound image may be displayed based on the stored gain profile.

Figure 10:
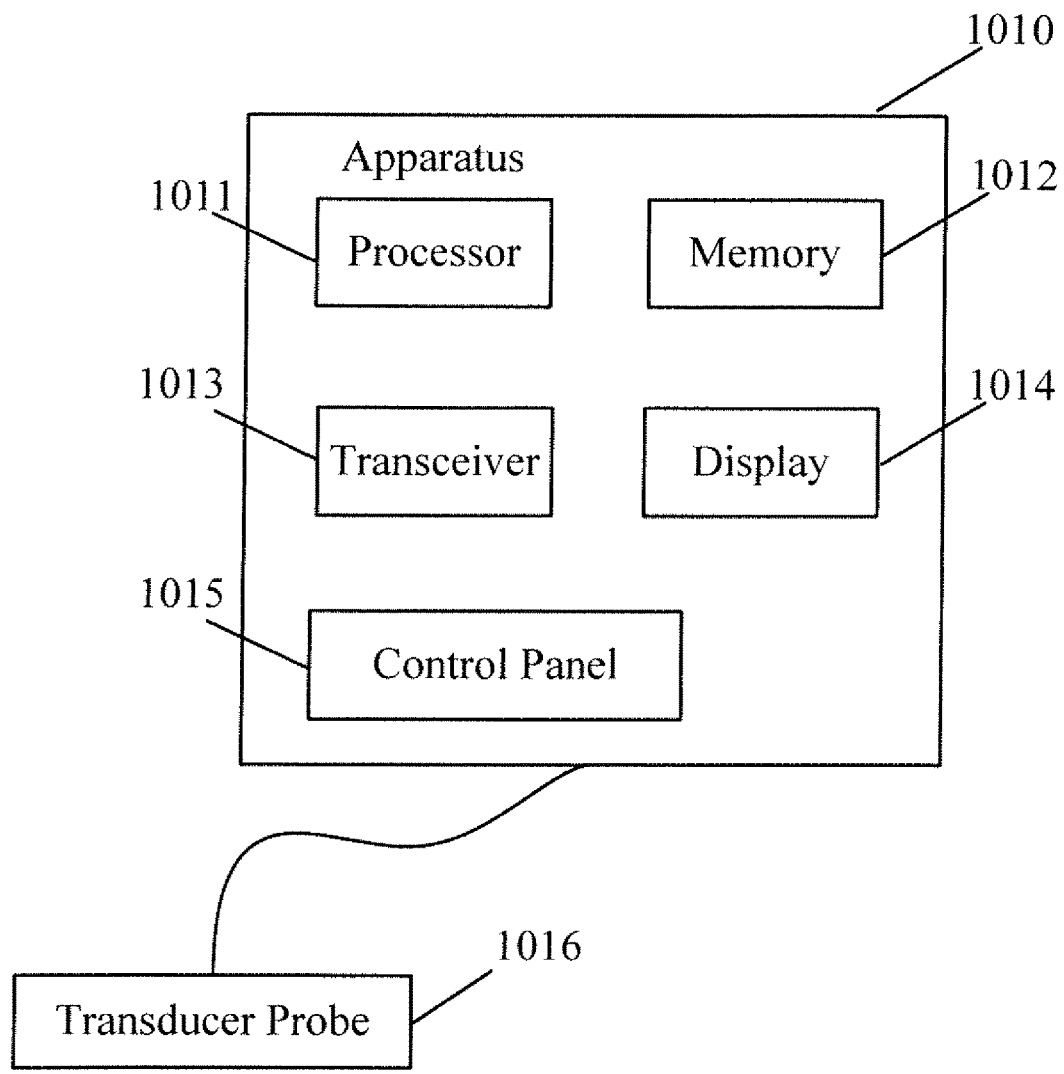
FIG. 10 is a diagram illustrating exemplary components of the system according to some embodiments of the disclosed subject matter.

FIG. 10 is an example of an apparatus according to some embodiments of the disclosed subject matter. In particular, FIG. 10 illustrates an apparatus or a medical imaging device 1010, such as an ultrasound system. The ultrasound system may in some embodiment be a portable point-of-care ultrasound, which may be hand held, portable, or cart-based. The ultrasound system may be any Fujifilm Sonosite® ultrasound product, for example Vevo®, S-Series®, Edge®, X-Porte®, or M-Turbo® ultrasound. It should be understood that each feature of FIGS. 1-9, and any combination thereof, can be implemented by an apparatus or an ultrasound system, using various hardware, software, firmware, and/or one or more processors or circuitry, in connection with various different embodiments of the disclosed subject matter.

In one embodiment, the apparatus can include at least one processor, control unit, inertial measurement unit, or module, indicated as 1011. At least one memory can also be provided in each apparatus, indicated as 1012. The memory can include computer program instructions or computer code contained therein, which instructions or code may be executed by the processor. The system may also include networked components communicating over a local network, a wide area network, wirelessly and/or wired, or by any other coupling that allows communication of data from one system component to another.

In certain embodiments one or more transceivers 1013 can be provided. The one or more transceivers 1013 may receive signals from transducer probe 1016, which transmits and/or receives sound waves to and from the body being examined. Transducer probe 1016 may transmit the signal to apparatus 1010 via a wireless or wired communication. In some embodiments, the one or more transceivers 1013 may be located on an analog front end (AFE). The AFE, for example, may include a linear low nose amplifier (LNA) and a voltage-controlled attenuator (VCAT). The time-gain control may be implemented at the AFE, before the signals are transmitted from transducer probe 1016 to apparatus 1010.

Transducer probe 1016 may be able to transmit sound waves of various frequencies and receive echo signals. The sound waves, for example, may range from a low bandwidth frequency of 3 Megahertz (MHz) to as high frequency of 71 MHz. Other embodiments may use any other soundwave frequency. Higher frequencies may allow for the imaging of shorter distances, while lower frequencies may allow for the imaging of longer distances, with each typically providing different resolutions. Transducer probe 1016 may in some embodiments also include a beamformer.

In some embodiments, transducer probe 1016 may be a single element or a multi-element transducer that is moved to sweep the transducer over a range of beam angles. Transducer probe 1016 may use either wired or wireless communication to send and/or receive information to apparatus 1010. The transmitted information may be saved in memory 1012, or in any other external memory or database.

The ultrasound system may also include any other component not shown in FIG. 10, such as an AFE that includes, for example, an LNA and VCAT, an analog to digital converter, and a beamformer receiver. Once the analog sound signal is received by the probe, it may be amplified on the front end of the ultrasound system, and converted into a digital format using any known analog to digital converter. Once converted into digital form, the signal may be transmitted to apparatus 1010. Apparatus 1010 may include or be connected to display 1014, which may display the received digital information. The time-gain control described in FIGS. 1-9 may adjust the image displayed on the ultrasound machine.

In certain embodiments, display 1014 may be located in a separate apparatus from apparatus or ultrasound machine 1010. In yet another example, instead of a display the apparatus may include a projector capable of projecting the image onto an external display or screen, or may include active eyeglasses or headset that may be worn by the operator of the ultrasound system in order to view the displayed data.

In some embodiments, apparatus 1010 may be a medical imaging device, such as an ultrasound system, configured to carry out the embodiments described above in relation to FIGS. 1-9. In certain embodiments, at least one memory including computer program code can be configured to, when executed by the at least one processor, cause the apparatus to perform any or all of the processes described herein. Processor 1011 can be embodied by any computational or data processing device, such as a central processing unit (CPU), digital signal processor (DSP), application specific integrated circuit (ASIC), programmable logic devices (PLDs), field programmable gate arrays (FPGAs), input/output (I/O) circuitry, digitally enhanced circuits, or comparable device, or any combination thereof. In one example, the ASIC described in U.S. Pat. No. 8,213,467 may be used. U.S. Pat. No. 8,213,467 is hereby incorporated by reference in its entirety. The processors can be implemented as a single controller, or a plurality of controllers or processors.

The ultrasound system may also include a system control panel 1015. System control panel 1015, such as the tactile gain control used in, for example, may include the user interface, touchpad, or touchscreen used to adjust the near, middle, and far middle gain control. The system control panel, may alternatively or in addition to, include other controls for adjusting or changing various settings of the ultrasound system.

For firmware or software, the implementation can include modules or a unit of at least one chip set (for example, including procedures and/or functions). Memory 1012 can independently be any suitable storage device, such as a non-transitory computer-readable medium, a hard disk drive (HDD), random access memory (RAM), flash memory, or other suitable memory. The memories can be combined on a single integrated circuit with a processor, or can be separate therefrom. Furthermore, the computer program instructions can be stored in the memory and be processed by the processors, and can be any suitable form of computer program code, for example, a compiled or interpreted computer program written in any suitable programming language. For example, in certain embodiments, a non-transitory computer-readable medium can be encoded with computer instructions or one or more computer programs (such as added or updated software routine, applet or macro) that, when executed in hardware, can perform a process such as one of the processes described herein. Computer programs can be coded by a programming language, which can be a high-level programming language, such as objective-C, C, C++, C#, Java, etc., or a low-level programming language, such as a machine language, or assembler. Alternatively, certain embodiments can be performed entirely in hardware.

The above embodiments provide significant technical improvements and advantages to medical imaging devices, such as an ultrasound system. Certain embodiments may provide a near, middle, and far gain control, which provides users with the ability to further customize the image being displayed on the ultrasound system. The middle gain control may be configured for two-dimensional range adjustment. The two-dimensional range adjustment allows for increased customization of the gain curve. As discussed above, in some embodiments the middle gain control may be rotated, which allows for even further customization of the gain curve. Providing the user with increased flexibility of the gain curve may allow a user to quickly and more accurately achieve the desired gain profile. The selected gain curve and gain profile can then determine the brightness of the ultrasound image shown by the user. The above embodiments therefore constitute significant technological improvements to all medical imaging devices, and in particular ultrasound systems.

The features, structures, or characteristics of certain embodiments described throughout this specification can be combined in any suitable manner in one or more embodiments. For example, the usage of the phrases "certain embodiments," "some embodiments," "other embodiments," or other similar language, throughout this specification refers to the fact that a particular feature, structure, or characteristic described in connection with the embodiment can be included in at least one embodiment of the disclosed subject matter. Thus, appearance of the phrases "in certain embodiments," "in some embodiments," "in other embodiments," or other similar language, throughout this specification does not necessarily refer to the same group of embodiments, and the described features, structures, or characteristics can be combined in any suitable manner in one or more embodiments.

One having ordinary skill in the art will readily understand that the disclosed subject matter as discussed above can be practiced with procedures in a different order, and/or with hardware elements in configurations which are different from those disclosed. Therefore, although the disclosed subject matter has been described based upon these embodiments, it would be apparent to those of skill in the art that certain modifications, variations, and alternative constructions would be apparent, while remaining within the spirit and scope of the disclosed subject matter.

What is claimed is:

1. An ultrasound system comprising:
   at least one memory storing computer program code; and
   at least one processor;
   wherein the computer program code is configured, when executed by the at least one processor, to cause the ultrasound system to:
   provide a tactile gain control comprising a near, middle, and far gain control, wherein the middle gain control is configured for two-dimensional range adjustment of depth and gain;
   adjust the middle gain control in a first dimension to adjust depth and a second dimension to adjust gain; and
   display an ultrasound image based on the adjusted middle gain control.

2. The ultrasound system of claim 1, wherein the computer program code is configured, when executed by the at least one processor, to cause the ultrasound system to:
   manipulate a received signal at the ultrasound system based on the adjusted middle gain control.

3. The ultrasound system of claim 2, wherein the received signal may be manipulated at a beginning and an end of the signal.

4. The ultrasound system of claim 1, wherein the computer program code is configured, when executed by the at least one processor, to cause the ultrasound system to:
   determine a gain curve based on the tactile gain control, wherein the ultrasound image is displayed based on the gain curve.

5. The ultrasound system of claim 4, wherein the computer program code is configured, when executed by the at least one processor, to cause the ultrasound system to:
   use interpolation to determine the gain curve, wherein the interpolation is based on at least one of a transducer type, an imaging mode, or an examination type.

6. The ultrasound system of claim 4, wherein the computer program code is configured, when executed by the at least one processor, to cause the ultrasound system to:
   rotate the middle gain control clockwise or counterclockwise to adjust a curvature of the gain curve.

7. The ultrasound system of claim 1, wherein the computer program code is configured, when executed by the at least one processor, to cause the ultrasound system to:
   activate the tactile gain control in response to a received user input, wherein the received user input is a sensed touching of the tactile gain control by a user.

8. The ultrasound system of claim 1, wherein the computer program code is configured, when executed by the at least one processor, to cause the ultrasound system to:
   display the tactile gain control on a user interface of the ultrasound system; and
   adjust the middle gain control based on a received user input, wherein the received user input is sensed touching of the user interface.

9. The ultrasound system of claim 1, wherein the computer program code is further configured to adjust at least one of the near or far gain control in a first dimension to adjust depth and a second dimension to adjust gain, and wherein each of the near, middle, or far gain controls can be individually adjusted.

10. The ultrasound system of claim 4, wherein the computer program code is configured, when executed by the at least one processor, to cause the ultrasound system to:
    display the gain curve joining the near, middle, and far gain control, wherein the displayed gain curve is different than an underlying gain curve used for manipulating a received signal at the ultrasound system.

11. The ultrasound system of claim 1, wherein the computer program code is configured, when executed by the at least one processor, to cause the ultrasound system to:
    receive a user input at the tactile gain control to perform a gain reset, wherein the gain reset returns the near, middle, and far gain control to a baseline setting.

12. The ultrasound system of claim 11, wherein the user input comprises double tapping a vertical gain reference line or a displayed gain curve on the tactile gain control.

13. The ultrasound system of claim 1, wherein the computer program code is configured, when executed by the at least one processor, to cause the ultrasound system to:
    adjust the gain using an overall gain control that is separate from the near, middle, or far gain control.

14. The ultrasound system of claim 1, wherein the computer program code is configured, when executed by the at least one processor, to cause the ultrasound system to:
    store a gain profile, wherein the gain profile comprises a position of the near, middle, and far gain control.

15. The ultrasound system of claim 14, wherein the computer program code is configured, when executed by the at least one processor, to cause the ultrasound system to:
    retrieve the stored gain profile based on a user selection; and
    display the ultrasound image based on the stored gain profile.

16. The ultrasound system of claim 4, wherein the computer program code is configured, when executed by the at least one processor, to cause the ultrasound system to:
    change a curve slope of the gain curve based on a received user input; and
    adjust a reach based on the changed curve slope.

17. A computer implemented method in an ultrasound system comprising:

providing a tactile gain control comprising a near, middle, and far gain control, wherein the middle gain control is configured for two-dimensional range adjustment of depth and gain;

adjusting the middle gain control in a first dimension to adjust depth and a second dimension to adjust gain; and displaying an ultrasound image based on at least one of the adjusted near, middle, or far gain control.

18. The computer implemented method in an ultrasound system according to claim 17, further comprising:

manipulating a received signal at the ultrasound system based on the adjusted middle, gain control.

19. The computer implemented method in an ultrasound system according to claim 17, further comprising:

determining a gain curve based on the tactile gain control, wherein the ultrasound image is displayed based on the gain curve.

20. The computer implemented method in an ultrasound system according to claim 19, further comprising:

rotating the middle gain control clockwise or counter-clockwise to adjust a curvature of the gain curve.

21. The ultrasound system of claim 4, wherein:

the gain curve is one of a parabola and a hyperbola; and the gain curve is drawn from a near gain control point to a far gain control point.

22. The computer implemented method in an ultrasound system of claim 19, wherein:

the gain curve is one of a parabola and a hyperbola; and the gain curve is drawn from a near gain control point to a far gain control point.

* * * * *